United States Patent [19]

Carpenter et al.

[11] Patent Number: 5,041,236

[45] Date of Patent: Aug. 20, 1991

[54] ANTIMICROBIAL METHODS AND COMPOSITIONS EMPLOYING CERTAIN LYSOZYMES AND ENDOGLYCOSIDASES

[75] Inventors: Richard S. Carpenter; Ann M. Wolff, both of Cincinnati, Ohio

[73] Assignee: The Procter & Gamble Company, Cincinnati, Ohio

[21] Appl. No.: 428,273

[22] Filed: Oct. 27, 1989

[51] Int. Cl.$^5$ .................... C11D 7/42; A61K 37/54; C12S 9/00; C12S 11/00

[52] U.S. Cl. ................ 252/174.12; 252/106; 252/DIG. 5; 252/DIG. 12; 252/DIG. 13; 252/DIG. 14; 424/94.61; 435/200; 435/206; 435/212; 435/264; 435/938

[58] Field of Search .............. 252/174.12, DIG. 12, 252/106; 435/195, 196, 200, 206, 208, 212, 227, 264, 938; 424/94.61, 94.62

[56] References Cited

U.S. PATENT DOCUMENTS

| 4,355,022 | 10/1982 | Rabussay | 424/50 |
|---|---|---|---|
| 4,619,825 | 10/1986 | Eigen et al. | 424/49 |
| 4,639,375 | 1/1987 | Tsai | 426/49 |
| 4,710,313 | 12/1987 | Miyajima et al. | 252/105 |
| 4,939,123 | 7/1990 | Neeser et al. | 514/8 |

FOREIGN PATENT DOCUMENTS

| 192401 | 8/1986 | European Pat. Off. . |
| 219220 | 4/1987 | European Pat. Off. . |
| 2937964 | 11/1982 | Fed. Rep. of Germany . |
| 8609459 | 12/1987 | France . |
| 49-048825 | 5/1974 | Japan . |
| 49048825 | 5/1974 | Japan . |
| 55-153709 | 11/1980 | Japan . |
| 57-075926 | 5/1982 | Japan . |
| 59-088086 | 5/1984 | Japan . |
| 61-015827 | 1/1986 | Japan . |
| 62-044180 | 2/1987 | Japan . |
| 62-248487 | 10/1987 | Japan . |
| 63-002911 | 1/1988 | Japan . |
| 8607738 | 4/1987 | South Africa . |
| 0867738 | 10/1986 | U.S.S.R. . |
| 1311375 | 3/1973 | United Kingdom . |
| 2120140 | 11/1983 | United Kingdom . |
| 8805992 | 8/1988 | World Int. Prop. O. . |

OTHER PUBLICATIONS

Thotakura et al., Methods in Enzymology, vol. 138, pp. 350-359, 1987.
Digan et al., "Biotechnology", vol. 7, pp. 160-164, 2/1989.
Hughes, 1983, Glycoproteins, pp. 23-26 (Chapman & Hall, New York, N.Y.).
Boehringer Mannheim, Indianapolis, IN catalogue "Glycohydrolases".
Chen, 1986, Plant Science, vol. 43, pp. 93-101.
Abeles et al., 1970, Plant Physiology, vol. 47, pp. 129-134.
Dobson et al., 1984, Part I, J. of Biol. Chem., vol. 259, No. 18, Sep. 25 issue, pp. 11607-11616.
Jollés et al., 1984, Part II, J. of Biol. Chem., vol. 259, No. 18, Sep. 25 issue, pp. 11617-11625.
Chaiet et al., 1970, Applied Microbiology, vol. 20, No. 3, pp. 421-426.
Montague, M.D., 1964, Biochim. Biophys. Acta, vol. 86, pp. 588-595.
Anderson et al., 1964, Biochem. J., vol. 90, pp. 30-35.
Geyer et al., 1984, Eur. J. Biochem., vol. 143, pp. 531-539.
Hsieh et al., 1983, The Journal of Biological Chemistry, vol. 258, No. 4, issue of Feb. 25, pp. 2555-2561.
Chipman et al., 1969, Science, vol. 165, pp. 454 $\propto$ 465.
Haskell et al., 1970, Journal of Medicinal Chemistry, vol. 13, No. 4, pp. 697-704.
Neuberger et al., 1967, Nature, vol. 215, pp. 524-525.
Tute, MS, 1970, Part II, vol. 13, pp. 48-51.
Chang et al., 1986, Molecular and Biochemical Parasitology, vol. 18, pp. 197-210.

Primary Examiner—Paul Lieberman
Assistant Examiner—A. Beadles-Hay
Attorney, Agent, or Firm—Kathleen M. Harleston; Donald E. Hasse; Thomas H. O'Flaherty

[57] ABSTRACT

An antimicrobial composition comprising endo-$\beta$-N-acetylglucosaminidase and/or endoglycopeptidase, and ruminant stomach lysozyme is presented. A method for destroying or removing microbes by treatment with these enzymes is also presented.

25 Claims, No Drawings

ANTIMICROBIAL METHODS AND COMPOSITIONS EMPLOYING CERTAIN LYSOZYMES AND ENDOGLYCOSIDASES

FIELD OF THE INVENTION

This invention relates to antimicrobial compositions and methods employing ruminant stomach lysozyme and certain endoglycosidases. More particularly, it relates to antimicrobial compositions, and methods for the destruction or removal of microbes by treatment with antimicrobial compositions, comprising ruminant stomach lysozyme, and endo-β-N-acetylglucosaminidase or endoglycopeptidase.

BACKGROUND OF THE INVENTION

Lysozyme is a mucopeptide glycohydrolase enzyme which hydrolyzes 1,4-B links between N-acetylmuramic acid and N-acetylglucosamine, and is thus destructive to cell walls of certain microbes. Commercially available lysozyme has been used in, for example, dentifrices, chewing gums, and contact lens cleaners.

Ruminant stomach lysozyme is a lysozyme characteristic of the stomach mucosa of mammals with foreguts. It is apparently not in wide commercial usage. Endo-β-N-acetylglucosaminidases have generally been used as analytical tools for the structural study of carbohydrates and or glycoproteins. We have found that the antimicrobial effectiveness of ruminant stomach lysozyme plus endo-β-N-acetylglucosaminidase and/or endoglycopeptidase is greater than the antimicrobial effectiveness of either enzyme alone.

The use of lysozyme in mixtures for use as antimicrobials has been noted in dental rinse (U.S. Pat. No. 4,355,022, Rabussay, issued Oct. 19, 1982). Rabussay discloses a method for removing plaque and calculus comprising applying a solution containing lysozyme (0.1 ml/mg), and optionally also applying lipases, phospholipases, carbohydrases, and/or proteases. A dental treatment agent comprising the mixture is also disclosed by Rabussay. Carbohydrase is a general class of enzymes to which endoglycosidase belongs.

Australian Patent 8548514, Neeser, May 1, 1986 discloses an antibacterial composition containing a glycopeptide (I) and/or oligosaccharide. In the preparation, a glycoprotein (A) of plant origin is digested with a proteolytic enzyme, then optionally the glycopeptide product is converted to oligosaccharides by treatment with endo-beta-N-acetylglucosaminidase-H. The product can then be digested with an exo-alpha-mannosidase to preferentially cleave the alpha 1-2 bonds between mannose residues. The isolated glycopeptide (I) is claimed to be effective against pathogenic bacteria having type I fimbriae (e.g. *Escherichia coli, Klebsiella pneumoniae, Salmonella typhimurium* or *Shigella flexneri*).

Japanese Patent 62 044 180, laid open Feb. 26, 1987 discloses an endo-β-N-acetylglucosaminidase (I) which reacts with the N,N'-diacetylchitobiose structure of asparagine-bonded sugar of glycoprotein to hydrolyze the beta-4 bond of N-acetylglucosamine and isolate oligosaccharide from glycoprotein. It has substrate specificity such that (I) reacts with high mannose type or mixed type of asparagine bonded saccharide chain and with complexed products. The enzyme is obtained from *Canavalia gladiata DC*. It is useful for researching bioactivity of the sugar chain portions of glycoproteins. Enhancement of ruminant stomach lysozyme action through endoglycosidase action has not been described, however.

Three copending U.S. patent applications filed on the same day as this patent application, describe methods and formulations comprising Type II endoglycosidases, a group which includes the instant endoglycosidases. The first copending patent application, entitled "Method and Formulation Employing Type II Endoglycosidase" and whose inventors are R. S. Carpenter, A. M. Wolff, P. J. Lad, and I. J. Goldstein, describes Type II endoglycosidases for removal of glycoside-containing substances. The second copending patent application, entitled "Method Employing Type II Endoglycosidase", whose inventors are R. S. Carpenter, A. M. Wolff, and P. J. Lad, describes Type II endoglycosidases for removal of microorganisms. The third copending patent application, entitled "Antimicrobial Method and Formulation Employing Type II Endoglycosidase and Antimicrobial Agent", whose inventors are R. S. Carpenter, A. M. Wolff, and P. J. Lad, describes the combination of Type II endoglycosidases and antimicrobial agents. The present patent application describes an exemplary benefit gained from combining ruminant stomach lysozyme with endo-β-N-acetylglucosaminidase and/or endoglycopeptidase.

SUMMARY OF THE INVENTION

This invention presents antimicrobial compositions comprising endo-β-N-acetylglucosaminidase and/or endoglycopeptidase, and ruminant stomach lysozyme. Preferred are Endo-H, D or F and PNGase F or A. A highly preferred lysozyme is bovine lysozyme which has been genetically engineered via the yeast, *Pichia pastoris*. It is preferred that the compositions comprise detergent surfactant. Methods for the destruction and/or removal of microbes by treatment with endo-β-N-acetylglucosaminidase and/or endoglycopeptidase, and ruminant stomach lysozyme, are also included.

DESCRIPTION OF THE INVENTION

The present invention relates to the combination of ruminant stomach lysozyme with certain endoglycosidases for surprising effectiveness against microbes. Antimicrobial compositions and methods employing the combination are included.

A. Endoglycosidases

Endoglycosidases are glycohydrolase enzymes which cleave internal glycosidic linkages in a substrate. The endoglycosidases for use herein are from two of the three major groups of endoglycosidases currently known. The first group, preferred herein, is endo-β-n-acetylglucosaminidase, which is specific for di-N-acetylchitobiose moieties in the core of asparagine ("Asn")-linked oligosaccharide chains. See Thotakura, NR et al., "Enzymatic Deglycosylation of Glycoproteins", *Methods in Enzymology*, vol. 138, pp. 350–359. The known endo-β-N-acetylglucosaminidases include Endo-D from *Diplococcus pneumoniae,* Endo-H from *Streptomyces griseus* and Endo-F from *Flavobacterium meningosepticum*. Endo-H has also been cloned in *Escherichia coli*, Robbins, PW et al. *Journal of Biological Chemistry,* vol. 259, p. 7517 (1984), and Bacillus.

The second group for use herein is endoglycopeptidase, called N-glycosidase or glycopeptidase or peptide N-glycosidase. These hydrolyze N-acetylglucosaminylasparagine linkages. The PNGase enzymes are endoglycopeptidases. The other type of endoglycopeptidase, peptide O-glycosidase (endo-N-acetyl-α-D-galactosaminidase from *D. pneumoniae*), which cleaves N-acetylgalactosaminylserine/threonine linkages, have narrow substrate specificities and are not of interest here.

The most useful PNGases for use herein are PNGase A from almond emulsin and PNGase F from *Flavobacterium meningosepticum*. These were only recently isolated and characterized. See *Methods in Enzymology*, above, vol. 138, p. 351.

The third major group of endoglycosidases is endo-β-N-galactosidase from *Diplococcus pneumoniae*, which hydrolyzes galactosidic bonds in poly(N-acetyl-galactosamine) type oligosaccharide prosthetic groups. *Methods in Enzymology*, above, vol. 138, p. 351. These are not of interest herein, nor are exo-glycosidases, which cleave external rather than internal glycosidic linkages.

Endo-β-N-acetylglucosaminidase and/or endoglycopeptidase is the first component of the instant compositions. Preferred for use herein are Endo-H, Endo-D, Endo-F, PNGase A, and PNGase F. More preferred are Endo-H, Endo-F, and PNGase F. Most preferred is Endo-H.

Although the endoglycosidases named immediately above are commercially available in purified form, they have mostly been used in the past in academic pursuits. Endo-βacetylglucosaminidases were used to define structural features of the carbohydrate chains of glycoproteins. Hughes, RC, *The Glycoproteins*, p. 24 (1983). They have heretofore generally not been practically available in large quantities and are not in use in consumer products.

Endo-H, Endo-F, Endo-D and PNGase F can be obtained from Boehringer Mannheim Biochemicals, Indianapolis, Ind. Endo-H, which has an optimum pH of 5.0, "hydrolyzes glycoproteins and glycopeptides with very high glycon specificity: requiring the tetrasaccharide Man α1→3 Man α1→6 Man β1→4 GlcNAc (the α-mannosyl residue at the non-reducing end can be substituted at the C-2 position by other sugars), and with higher glycon specificity than D-enzyme. It hydrolyzes the sugar chains with N-acetylglucosamine, N-acetylglucosaminitol and GlcNAc→Asn as aglycon moieties, but cannot act on those with Fuc α1→6 GlcNAc and Fuc α1→6 GlcNAc→Asn." *Biochemica Information*, 1987, Boehringer Mannheim, under "Endo-H". Endo-H cloned of *S. plicatus* from *S. lividans*, with an optimum pH of between 5.0 and 7.5 and the same substrate specificity as above, is also commercially available.

Endo-D, which has an optimum pH of 6.5, "hydrolyzes glycoproteins and glycopeptides with very high glycon specificity; requiring the trisaccharide Man α1→3 Man β1→4 GlcNAc (the α-mannosyl residue at the non-reducing end should not be substituted by other sugars), and with rather broad aglycon specificity: it hydrolyzes sugar chains which are linked to N-acetylglucosamine, Fuc α1→6 GlcNAc, GlcNAc→Asn, and Fuc α1→6 GlcNAc→Asn as well." *Biochemica Information*, 1987, Boehringer Mannheim, under "Endo-D".

Endo-F, which has an optimum pH of 5.0, "cleaves N-glycans within chitobiose, leaving a molecule of N-acetyl-glucosamine on the asparagine. It specifically cleaves N-glycans from 'high mannose' types. It also cleaves some 'hybrid' and complex biantennary N-glycans at a much slower rate. Tri- and tetra-antennary complex N-glycans are not cleaved." *Biochemica Information*, 1987, Boehringer Mannheim, under "Endo-F".

Endo-F is also available as a mixture with PNGase F. For this mixture, "the enzyme activities are controlled by pH". At pH 4.0, only Endo-F activity "is functional, releasing octapeptide-GlcNAc and oligosaccharide-GlcNAc from ovalbumin. At pH 9.3, the predominant cleavage is by peptide: N-glycosidase F . . . at the glycosylamine bond, releasing octapeptide and oligosaccharide-GlcNAc-GlcNAc. This latter oligosaccharide is then hydrolyzed by Endo-F to oligosaccharide-GlcNAc plus GlcNAc." *Biochemica Information*, 1987, Boehringer Mannheim, under "Endo-F".

PNGase F, with an optimum pH between 5.0 and 7.0, hydrolyzes "types of N-glycans between asparagine and the carbohydrate moiety, provided that both the amino and carboxyl groups are present in the peptide bond." See *Biochemica Information*, 1987, Boehringer Mannheim, under "PNGase F".

According to Thotakura et al., *Methods in Enzymology*, vol. 138, pages 354–355, the pH optimum for Endo-H, Endo-F, and PNGase A is between 4 and 5, while the optimum for PNGase F is about 8.5. They state that citrate completely inhibits PNGase F activity, that nonionic detergents stabilize these endoglycosidases, and that PNGases A and F have similar substrate specificities, although PNGase F is apparently more potent.

Both Endo-H and Endo-F cleave high mannose structures. Endo-F can also cleave biantennary complex structures at a slower rate, but does not cleave oligosaccharide chains with bisect B-1,4-N-acetylglucosamine. Methods in Enzymology, vol. 138, p. 355.

The substrate for Endo-H and F is:

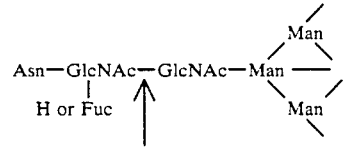

The cleavage site is indicated by the arrow. GlcNAc is N-acetyl glucuronic acid.

Endo-H has been reported to cleave lipid-linked oligosaccharides, Chalifour, R. J. et al. (1983), *Archives of Biochemistry and Biophysics*, vol. 229, pp. 386–394, and di-N-acetylchitobiose linkages in oligosaccharides and glycoproteins, Tarenton, A. L. et al. (1974), *Journal of Biological Chemistry*, vol 249, pp. 811–817.

The substrate for PNGase F is:

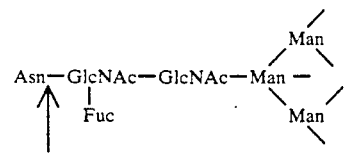

The site of cleavage is indicated by the arrow. PNGases F and A can cleave high mannose structures, or complex multibranched oligosaccharide chains including tri- and tetraantennary structures, except when they are on the amino or carboxy termini. *Methods in Enzymology*, vol. 138, p. 355. PNGase F requires at least a di-N-acetylchitobiose core. Laemmli, U. K., *Nature* vol. 227, p. 680 (1970).

The concentration of the endoglycosidase and the amount of incubation time necessary in order for deglycosylation to occur depend upon the type of substrate.

The subject endoglycosidases have recently been shown to remove glycoside-containing substances and disrupt and/or remove microorganisms, especially fungi, from surfaces, and to provide a surprising benefit with other antimicrobial agents.

Since endoglycosidase is a current research topic, it is predictable that new endoglycosidases will be found and cloned with the same or similar activity as the above. Those which act with ruminant stomach lysozyme as described herein are intended to be included in this invention.

B. Ruminant Stomach Lysozyme

The second component in the instant compositions is stomach lysozyme from ruminants, including bovine lysozyme. A ruminant is a cud-chewing mammal with a rumen (foregut). In the foregut, which acts as an anaerobic fermentation chamber, are microbes which digest cellulose. Vaughan, T. A., *Mammalogy*, 2nd ed., WB Saunders Co., Philadelphia, 1978. Many of these microbes enter the stomach, where they are digested. A specific type of enzyme, found at high levels in ruminant stomach mucosa, which helps to digest these microbes is lysozyme c. Dobson, DE et al., "Stomach Lysozymes of Ruminants", *Journal of Biological Chemistry*, vol. 259. pp. 11607–11625 (1984), incorporated herein. Lysozyme c is unusually resistant to inactivation by pepsin and is said to function at a lower pH than other non-ruminant lysozymes. *Journal of Biological Chemistry*, vol. 259, pp. 11607, 11617. Evidence has been found that these ruminant stomach lysozymes c are significantly different functionally than conventional mammalian lysozymes c, presumably as a result of evolution in the specialized ruminant stomach environment. *Journal of Biological Chemistry*, vol. 259, p. 11608.

Ruminant stomach lysozyme c is preferred for use herein. More preferred are the three closely related lysozymes c (1, 2 & 3) isolated from cow stomach mucosa and described in *The Journal of Biological Chemistry*, vol. 259, pp. 11619–11625, including supplementary material, incorporated herein. These resemble lysozymes c of known amino acid compositions in having eight ½-cystine residues and a high proportion of tryptophan, although lysozymes c differ from other known lysozymes c in their low arginine content. *Journal of Biological Chemistry*, vol. 259, p. 11625 supp. The amino acid sequence of 129 amino acids has been determined for one of the three closely related cow stomach lysozymes c, called c2. It differs from the other known lysozymes c at 39–60 positions, including one amino acid deletion. *Journal of Biological Chemistry*, vol. 259, p. 11617. Of the three cow stomach lysozymes, the most preferred herein is cow stomach lysozyme c2. Cow, or bovine, lysozyme c2 has a molecular weight of 14,398. *Journal of Biological Chemistry*, vol. 259, p. 11626, supplementary material.

Bovine stomach lysozyme c2 has a higher resistance to proteases and a more acidic and narrow pH range than chicken hen egg white lysozyme. *Journal of Biological Chemistry*, vol. 259, p. 11607. Bovine (cow stomach) lysozyme, although not currently in wide commercial usage, has been proposed as an antibacterial agent at acidic pHs or as an animal feed additive. Digan, ME et al., "Continuous Production of a Novel Lysozyme via Secretion from the Yeast, *Pichia pastoris*", *Biotechnology*, vol. 7, pp. 160–164 (1989), which is incorporated herein.

Recently, bovine lysozyme c2 has been genetically engineered from the yeast *Pichia pastoris*. The Salk Institute Biotechnology/Industrial Associates, Inc. of LaJolla, Calif. genetically engineered this lysozyme by cloning a cDNA for bovine lysozyme c2, and expressing its protein product by secretion using its native signal sequence in *Pichia pastoris*. *Biotechnology*, vol. 7, p. 160. Biological activity of the recombinant product is said to be maintained, and it is expected that cost-efficient, high volume product will be produced. *Biotechnology*, vol. 7, pp. 160, 163.

Recombinant bovine lysozyme, especially from the yeast *Pichia pastoris*, is most preferred for use herein. Bovine lysozyme c2 genetically engineered from *Pichia pastoris* is especially versatile because it is surfactant-stable. Other ruminant stomach lysozymes which may be found and/or cloned are also contemplated by this invention, where they provide a benefit when combined with endo-$\beta$-N-acetylglucosaminidase or endoglycopeptidase.

Gram-positive bacteria are said to be more susceptible to lysozyme action than Gram-negative bacteria. *Staphylococcus aureus* is one Gram-positive bacteria, though, which is less susceptible to lysozyme, probably because it has different sugars in its cell wall glycopeptide. Davis et al. (1968) *Principles of Microbiology and Immunology*, Harper & Row, New York, pp. 118–119. In the instant invention, the combination of endo-$\beta$-N-acetylglucosaminidase and/or endoglycopeptidase (preferably Endo-H) and ruminant stomach lysozyme (preferably recombinant bovine lysozyme from *Pichia pastoris*) does severely disrupt *S. aureus* bacteria (see Examples). In addition, the above combination unexpectedly and significantly reduces colonies of *Escherichia coli*, a common Gram-negative organism, even though the enzymes separately do not (see Examples) Even for *Staphylococcus epidermidis*, a Gram-positive bacteria adversely affected by lysozyme or Endo-H separately, the combination of the two enzymes has a greater adverse effect than either enzyme alone. In addition to bacteria, the instant compositions are effective against fungus and yeast, although it is believed that this is attributable to the endoglycosidase, especially Endo-H, rather than only to the combination of the endoglycosidase with lysozyme.

C. Compositions

Included herein are antimicrobial compositions comprising ruminant stomach lysozyme, and endo-$\beta$-N-acetylglucosaminidase and/or endoglycopeptidase. Preferred are ruminant stomach lysozymes c and one or more of the following: Endo-H, Endo-F, Endo-D, PNGase A, and PNGase F. More preferred are bovine lysozyme c2 and Endo-H or PNGase F. Most preferred are recombinant bovine lysozyme from *Pichia pastoris* and Endo-H.

It is preferred that the weight ratio of ruminant stomach lysozyme to endo-$\beta$-N-acetylglucosaminidase or endoglycopeptidase be from about 1:4 to 4:1, preferably from about 2:1 to 1:2. For Endo-H and recombinant bovine lysozyme from *Pichia pastoris*, a 1:1 ratio is most preferred.

The compositions herein preferably comprise from about 1 to 1000 ppm, preferably from about 50 to 400 ppm, of the ruminant stomach lysozyme, and from about 1 to 1200 ppm, preferably from about 50 to 400 ppm, of the endo-$\beta$-N-acetylglucosaminidase or endoglycopeptidase. The compositions herein most preferably comprise from about 80 to 150 ppm Endo-H and from about 80 to 150 ppm of the recombinant bovine lysozyme.

The antimicrobial compositions herein are preferably in the form of a mouthwash, denture cleaner, dentifrice, laundry detergent, preservative, liquid soap, contact lens cleanser, or skin cleanser. These are described in more detail below. More preferably the compositions are in the form of a denture cleaner, dentifrice, mouthwash, preservative, liquid soap or laundry detergent. Most preferred is a laundry detergent, particularly a heavy-duty liquid laundry detergent.

The antimicrobial compositions herein preferably comprise from about 0.1 to 60 weight % detergent surfactant. The detergent surfactants are anionic, nonionic, cationic, ampholytic and/or zwitterionic surfactants, preferably nonionic and/or anionic surfactant. Nonionic surfactant is most preferred.

The instant compositions can be formulated as laundry detergents such as those disclosed in U.S. Pat. Nos. 4,507,219, 4,318,818, 4,605,509 and 4,412,934; hard surface cleaners such as those disclosed in U.S. Pat. Nos. 4,414,128, 3,679,608, 3,985,668 and 4,005,027; bar soaps such as those disclosed in U.S. Pat. Nos. 3,993,772 and 3,070,547; shampoos such as those disclosed in U.S. Pat. Nos. 4,345,080, 4,704,272 and 4,741,855; anti-acne products and oral compositions such as those disclosed in U.S. Pat. No. 4,684,518. These are incorporated by reference herein.

Where the antimicrobial composition is a preferred mouthwash, denture cleaner, or dentifrice, it preferably comprises from about 1 to 150 ppm each of Endo-H or PNGase F and bovine lysozyme c2. The same would apply where the antimicrobial composition is a contact lens cleaner.

Where the antimicrobial composition is a liquid or granular laundry detergent, it preferably comprises from about 2 to 250 ppm each of Endo-H and recombinant bovine lysozyme c2, and from about 1 to 90 weight % detergent surfactant selected from the group consisting of anionic, nonionic, cationic, ampholytic and zwitterionic surfactants. Preferably, from about 5 to 50, most preferably 10 to 40, weight % of the above detergent surfactant is included in preferred laundry detergent compositions.

Surfactants useful in the detergent compositions herein include well-known synthetic anionic, nonionic, cationic amphoteric and zwitterionic surfactants. Typical of these are the alkyl benzene sulfonates, alkyl- and alkylether sulfates, paraffin sulfonates, olefin sulfonates, alkoxylated (especially ethoxylated) alcohols and alkyl phenols, amine oxides, alphasulfonates of fatty acids and of fatty acid esters, alkyl betaines, and the like, which are well known from the detergency art. In general, such detersive surfactants contain an alkyl group in the $C_9$-$C_{18}$ range. The anionic detersive surfactants can be used in the form of their sodium, potassium or triethanolammonium salts; the nonionics generally contain from about 5 to about 17 ethylene oxide groups. $C_{11}$-$C_{16}$ alkyl benzene sulfonates, $C_{12}$-$C_{18}$ paraffin-sulfonates and $C_{10}$-$C_{16}$ alkyl sulfates containing from 0 to about 4 ethylene oxide units are especially preferred in the compositions of the present type.

A detailed listing of suitable surfactants for the compositions herein can be found in U.S. Pat. No. 3,936,537, Baskerville, issued Feb. 3, 1976, incorporated by reference herein. Commercial sources of such surfactants can be found in McCutcheon's *Emulsifiers and Detergents,* North American Edition, 1984, McCutcheon Division, MC Publishing Company, also incorporated herein by reference.

Useful detergency builders for the detergent compositions herein include any of the conventional inorganic and organic water-soluble builder salts, as well as various water-insoluble and so-called "seeded" builders. The instant laundry detergent compositions preferably comprise from about 1% to about 75%, more preferably from about 5% to about 40%, most preferably from about 10% to about 20%, by weight of detergent builders.

Nonlimiting examples of suitable water-soluble, inorganic alkaline detergent builder salts include the alkali metal carbonates, borates, phosphates, polyphosphates, tripolyphosphates, bicarbonates, silicates and sulfates. Specific examples of such salts include the sodium and potassium tetraborates, bicarbonates, carbonates, tripolyphosphates, pyrophosphates, and hexametaphosphates.

Examples of suitable organic alkaline detergency builder salts are: (1) water-soluble amino polyacetates, e.g., sodium and potassium ethylenediaminetetraacetates, nitrilotriacetates, and N-(2-hydroxyethyl)nitrilodiacetates; (2) water-soluble salts of phytic acid, e.g., sodium and potassium phytates; (3) watersoluble polyphosphonates, including sodium, potassium and lithium salts of ethane-1-hydroxy-1,1-diphosphonic acid, sodium, potassium, and lithium salts of methylenediphosphonic acid and the like.

Seeded builders include such material as sodium carbonate or sodium silicate, seeded with calcium carbonate or barium sulfate. Hydrated sodium zeolite A having a particle size less than about 5 microns is particularly desirable.

A detailed listing of suitable detergency builders can be found in U.S. Pat. No. 3,936,537, incorporated herein by reference. Preferred builders are fatty acids, polycarbonates, polyphosphates and mixtures thereof.

Optional detergent composition components include enzymes (e.g., proteases and amylases), peroxygen bleaches and bleach activators, halogen bleaches (e.g., sodium and potassium dichloroisocyanurates), soil release agents (e.g., methylcellulose), soil suspending agents (e.g., sodium carboxymethylcellulose), fabric brighteners, enzyme stabilizing agents, color speckles, suds boosters or suds suppressors, anticorrosion agents, dyes, fillers, germicides, pH adjusting agents, nonbuilder alkalinity sources, and the like.

The antimicrobial composition may also be a preservative, as, for example, in a shampoo or cosmetic such as face cream, or a food or beverage. It is preferably used in a cosmetic or shampoo in the amount of from about 50 to 400 ppm each of bovine lysozyme c2 and Endo-H (preferably) or PNGase F.

Compositions of this invention may be in the form of a shampoo. These shampoos typically comprise from about 5% to about 60 weight % of a synthetic surfactant, and the balance water. Suitable surfactants include ammonium lauryl sulfate, ammonium laureth sulfate, triethylamine lauryl sulfate, triethanolamine lauryl sulfate, triethanolamine laureth sulfate, monoethanolamine lauryl sulfate, mono-ethanolamine laureth sulfate, diethanolamine lauryl sulfate, diethanolamine laureth sulfate, lauric monoglycerdie sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, monoethanolamine cocoyl sulfate, monoethanolamine lauroyl sulfate, sodium tridecyl benzene sulfonate and sodium dodecyl benzene sulfonate.

These shampoos can contain a variety of optional components. Such conventional optional ingredients are well known to those skilled in the art, e.g., preservatives, such as benzyl alcohol, ethyl paraben, propyl paraben and imidazolidinyl urea; cationic surfactants, such as cetyl trimethyl ammonium chlorides, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as diethanolamide of a long-chain fatty acid (e.g., PRG 3 lauramide), block polymers of ethylene oxide and propylene oxide, sodium chloride, sodium sulfate, polyvinyl alcohol, ethyl alcohol and water-soluble polymers such as xanthan gum, hydroxyethyl cellulose, guar gum and starch; pH adjusting agents, such as citric acid, succinic acid, phosphoric acid, sodium hydroxide, sodium carbonate; perfumes; dyes; and/or sequestering agents, such as disodium ethylenediamine tetraacetate. Such agents generally are used individually at a level of from about 0.01% to about 10%, preferably from about 0.5% to about 5.0%, by weight of the composition.

Where the antimicrobial composition is a liquid hand soap, it comprises from about 50 to 400 ppm each of Endo-H or PNGase F and bovine lysozyme c2, and from about 10 to 40 weight % detergent surfactant (as described above for detergent compositions).

The antimicrobial composition may be a skin cleanser, preferably comprising from about 80 to 150 ppm each of Endo-H and recombinant bovine lysozyme from *Pichia pastoris*.

Additional ingredients which are incompatible with these enzymes should not be used. The pH of these compositions is preferably 5-8, more preferably 5.5-7, most preferably 6.5-7.5. The enzymes should be added to the composition in a manner which does not bring about their inactivation.

D. Methods

Along with antimicrobial compositions, methods for the destruction or removal of microbes are included herein. These methods comprise treatment with ruminant stomach lysozyme and endo-β-N-acetylglucosaminidase and/or endoglycopeptidase, preferably by application of a composition comprising these enzymes. Preferred are ruminant stomach lysozymes c and an endoglycosidase selected from the group consisting of Endo-H, Endo-F, Endo-D, PNGase A, and PNGase F. The treatment composition preferably comprises bovine lysozyme c2, and Endo-H and/or PNGase F. Most preferred are recombinant bovine lysozyme from *Pichia pastoris* and Endo-H. The preferred treatment comprises application of a composition comprising Endo-H and/or PNGase F, and recombinant bovine lysozyme from *Pichia pastoris*.

These enzymes should be used at a concentration sufficient to produce an antimicrobial effect. The amount of endoglycosidase or lysozyme in the treatment is generally less than the amount required for the same enzyme to produce the same antimicrobial effect if used alone. Without meaning to be bound by theory, it is believed that there is a synergism between the two types of enzymes; i.e. the effect of the endoglycosidase herein and the lysozyme, especially Endo-H and recombinant bovine lysozyme c2, is more than additive.

The instant method is preferably for the destruction or removal of bacteria, most preferably Gram-positive bacteria, preferably by a composition comprising from about 1 to 1200 ppm (preferably about 50 to 400 ppm) endo-β-N-acetylglucosaminidase or endoglycopeptidase (most preferably Endo-H), and from about 1 to 1000 ppm (preferably about 50 to 400 ppm) ruminant stomach lysozyme c (most preferably recombinant bovine lysozyme from *Pichia pastoris*). It is expected that the instant method is also effective against fungus and yeast, although that is likely attributable to the Endo-H rather than the combination with lysozyme.

The ratio of the ruminant stomach lysozyme to endo-β-N-acetyl- glucosaminidase/endoglycopeptidase is from about 1:4 to 4:1, preferably from about 1:2 to 2:1, most preferably about 1:1.

The instant method (and composition) is most preferably for the destruction of *Staphylococcus aureus* and/or *Escherichia coli*, preferably by a composition comprising from about 50 to 400 ppm, most preferably from about 100 to 150 ppm, each of Endo-H and recombinant bovine lysozyme.

The method preferably is comprised of washing or rinsing a surface containing microbes with a composition comprising ruminant stomach lysozyme and endo-β-N-acetylglucosaminidase and/or endoglycopeptidase. Depending upon the type of surface and treatment being applied, the surface may then be rinsed with water and/or hand-wiped, as with a cloth. The surface holding the microbes may be, for example, teeth or dentures, the oral cavity, fabrics, skin or contact lenses. The composition is preferably a mouthwash, denture cleaner, dentifrice, laundry detergent, preservative, contact lens cleaner, liquid soap, or skin cleanser (see above), more preferably a denture cleaner, mouthwash, preservative, liquid soap or laundry detergent, most preferably a laundry detergent, and particularly a heavy duty liquid laundry detergent. The composition preferably comprises from about 1 to 90, more preferably about 5 to 50, most preferably 10 to 40, weight % detergent surfactant selected from the group consisting of anionic, nonionic, cationic, ampholytic and zwitterionic surfactant, preferably anionic and/or nonionic surfactant. The method should be performed in a manner which does not bring about deactivation of the enzymes.

The compositions herein can also be used periodically for removal and prevention of microbial growth, for example, daily use of mouthwash compositions herein. It may be desirable to allow the antimicrobial compositions herein to reside in the area being treated for a certain period of time after application as in, for example, rinsing for 30 seconds with the mouthwash compositions herein.

The following examples illustrate the compositions and methods of the present invention. They are not meant to be construed as limiting the scope of the invention. All parts, percentages, and ratios herein are by weight unless otherwise specified.

EXAMPLE I

Effect of Bovine Lysozyme and Endo-H on *E. coli*

Samples from a 4-hour broth culture of *Escherichia coli* are treated with the following for 2 hours:
1) 0.2M Na citrate buffer, pH 7.0;
2) 0.2M Na citrate buffer, pH 7.0 plus 200 ppm each of bovine lysozyme and Endo-H, pH 7.0;
3) #1 plus 200 ppm of bovine lysozyme, pH 7.0;
4) #1 plus 200 ppm of Endo-H, pH 5.5.

The bovine lysozyme is recombinant bovine lysozyme from *Pichia pastoris*. It is believed that this bovine lysozyme alone or in combination with Endo-H functions best at pH 7.0. The Endo-H is recombinant Endo-H from *E. coli*. It is believed that Endo-H alone functions optimally at pH 5.5.

Serial dilutions of the treatment samples are plated, incubated overnight at 37° C., and counted for colonies.
Final colony counts for the treatments are as follows:

| | | |
|---|---|---|
| 1) | Buffer alone | $1.5 \times 10^6$ colonies |
| 2) | Bovine Lysozyme/Endo-H | $5.2 \times 10^4$ colonies |
| 3) | Bovine Lysozyme alone | $1.8 \times 10^6$ colonies |
| 4) | Endo-H alone | $1.2 \times 10^6$ colonies |

The above experiment is repeated with 100 ppm each of bovine lysozyme and Endo-H in #2.
1) 0.2M Na citrate buffer, pH 7.0;
2) 0.2M Na citrate buffer, pH 7.0 plus 100 ppm each of bovine lysozyme and Endo-H, pH 7.0;
3) #1 plus 200 ppm of bovine lysozyme, pH 7.0;
4) #1 plus 200 ppm of Endo-H, pH 5.5.
Final colony counts for the treatments are as follows:

| | | |
|---|---|---|
| 1) | Buffer alone | $0.3 \times 10^6$ colonies |
| 2) | Bovine Lysozyme/Endo-H | $3.8 \times 10^3$ colonies |
| 3) | Bovine Lysozyme alone | $6.6 \times 10^5$ colonies |
| 4) | Endo-H alone | $8.7 \times 10^5$ colonies |

In summary, bovine lysozyme and Endo-H are significantly more effective against *E. coli* than bovine lysozyme alone or Endo-H alone. The combination provides a two to three log reduction in bacteria over either enzyme alone or the buffer. The combination also provides benefits for different incubation time periods, for example from 30 minutes to 7 hours.

EXAMPLE II

Effect of Bovine Lysozyme and Endo-H on *S. epidermidis*

Samples from a 4-hour broth culture of *Staphylococcus epidermidis* are treated with the following for 6 hours:
1) 0.2M Na citrate buffer, pH 7.0;
2) 0.2M Na citrate buffer, pH 7.0 plus 100 ppm each of bovine lysozyme and Endo-H, pH 7.0;
3) #1 plus 100 ppm of bovine lysozyme, pH 7.0;
4) #1 plus 100 ppm of Endo-H, pH 5.5.

The bovine lysozyme is recombinant bovine lysozyme from *Pichia pastoris*. It is believed that this bovine lysozyme alone or in combination with Endo-H functions best at pH 7.0. The Endo-H is recombinant Endo-H from *E. coli*. It is believed that Endo-H alone functions optimally at pH 5.5.

Serial dilutions of the treatment samples are plated, incubated overnight at 37° C., and counted for colonies.
Final colony counts for the treatments are as follows:

| | | |
|---|---|---|
| 1) | Buffer alone | $1.1 \times 10^5$ colonies |
| 2) | Bovine Lysozyme/Endo-H | $5.8 \times 10^3$ colonies |
| 3) | Bovine Lysozyme alone | $1.0 \times 10^4$ colonies |
| 4) | Endo-H alone | $3.9 \times 10^4$ colonies |

In summary, bovine lysozyme and Endo-H (100 ppm each) are significantly more effective against *S. epidermidis* than bovine lysozyme alone (100 ppm) or Endo-H alone (100 ppm). The combination also provides benefits for different incubation time periods, for example from 30 minutes to 7 hours.

EXAMPLE III

Effect of Endo-H/Bovine Lysozyme on *S. aureus* Morphology

A 4-hour broth culture of *Staphylococcus aureus* (ATCC #6341) is divided and treated with the following actives for 2 hours at 7° C.:
1) 0.2M Na citrate buffer, pH 7.0;
2) #1 plus bovine lysozyme, 200 ppm, and Endo-H, 200 ppm, pH 7.0;
3) #1 plus bovine lysozyme, 400 ppm, pH 7.0;
4) #1 plus Endo-H, 400 ppm, pH 7.0.

Following treatment, the samples are placed on formar-coated grids, and examined by transmission electron microscopy. According to the micrographs, neither the buffer-control nor either of the enzymes alone disrupt the *S. aureus* microorganism. When the enzymes are combined, however, the treated microorganisms are severely condensed and/or disrupted.

EXAMPLE IV

Effectiveness of Bovine Lysozyme/Endo-H Over Other Lysozymes/Endo-H

A log-phase culture of *Escherichia coli* (083 K.H. 81) is divided and treated with different lysozyme/Endo-H combinations for 2 and 4 hours at 37° C.

At the end of the treatment times, aliquots of each are serially-diluted into phosphate buffered saline, and plated on Trypticase soy agar. The plates are incubated overnight at 37° C., and read for colony count. Results:

| | Treatment | Time | Colony Count |
|---|---|---|---|
| a) | 0.2 M Na citrate buffer, pH 7.0 | 2 hrs. | $1.8 \times 10^6$ |
| b) | 0.2 M Na citrate buffer +200 ppm bovine lysozyme, pH 7.0 | 2 hrs. | $1.9 \times 10^6$ |
| c) | 0.2 M Na citrate buffer +200 ppm bovine lysozyme +200 ppm Endo-H, pH 7.0 | 2 hrs. | $2.3 \times 10^3$ |
| d) | 0.2 M Na citrate buffer +200 ppm mutanolysin +200 Endo-H, pH 7.0 | 2 hrs. | $2.6 \times 10^6$ |
| e) | 0.2 M Na citrate buffer +200 ppm hen egg white lysozyme +200 ppm Endo-H, pH 7.0 | 2 hrs. | $1.0 \times 10^6$ |
| f) | 0.2 M Na citrate buffer, pH 7.0 | 4 hrs. | $1.5 \times 10^6$ |
| g) | 0.2 M Na citrate buffer +200 ppm bovine lysozyme, pH 7.0 | 4 hrs. | $1.8 \times 10^6$ |
| h) | 0.2 M Na citrate buffer +200 ppm bovine lysozyme +200 ppm Endo-H, pH 7.0 | 4 hrs. | $5.2 \times 10^3$ |

-continued

| | Treatment | Time | Colony Count |
|---|---|---|---|
| i) | 0.2 M Na citrate buffer +200 ppm mutanolysin +200 Endo-H, pH 7.0 | 4 hrs. | $2.5 \times 10^6$ |
| j) | 0.2 M Na citrate buffer +200 ppm hen egg white, pH 7.0 lysozyme +200 ppm Endo-H | 4 hrs. | $1.0 \times 10^6$ |

These results show that the combination of bovine lysozyme and Endo-H gives significant bacterial reduction. This reduction is far greater than any other lysozyme/Endo-H combination tested.

When the experiment is repeated with double the control concentration, e.g., 400 ppm of the various lysozymes alone, the combination of bovine lysozyme and Endo-H still gives bacterial reduction.

EXAMPLE V

Laundry Detergent Endo-H and Bovine Lysozyme

A heavy-duty liquid laundry detergent composition of the present invention is as follows:

| Component | Active Weight % |
|---|---|
| $C_{13}$ linear alkylbenzene sulfonic acid | 8.0 |
| $C_{14-15}$ alkyl polyethoxylate (2.25) sulfonic acid | 12.0 |
| 1,2 propanediol | 3.5 |
| Sodium diethylenetriamine pentaacetate | 0.3 |
| Monoethanolamine | 2.0 |
| $C_{12-13}$ alcohol polyethoxylate (6.5) | 5.0 |
| Ethanol | 8.5 |
| Sodium hydroxide | 3.85 |
| Potassium hydroxide | 1.8 |
| $C_{12-14}$ fatty acid | 10.0 |
| Citric acid | 4.0 |
| Calcium formate | 0.12 |
| $C_{12}$ alkyltrimethylammonium chloride | 0.5 |
| Tetraethylene pentamine ethoxylate (15-18) | 2.0 |
| Water | 37.12 |
| Dye | 0.08 |
| Perfume | 0.25 |
| Protease* | 0.125 |
| Endo-H | 125 ppm |
| Bovine Lysozyme** | 125 ppm |

*mg active enzyme/g (@ 34 mg active enzyme/g stock)
**4.0 units/microgram ±25%

The ingredients listed above are added to a mixing tank with a single agitator. Before the enzymes, dye and perfume are added, the pH of the mix is adjusted so that a 10% by weight solution in water at 20° C. has a pH of ~8.5.

This composition provides removal and prevention of microbes, especially bacteria, associated with laundry soils when tested immediately upon production. This removal and prevention is better than is provided by the heavy duty liquid detergent without Endo-H/bovine lysozyme.

EXAMPLE VI

Shampoo With Preservative

| Component | Level |
|---|---|
| Ammonium alkyl sulfate (29% aqueous solution) | 55.25% |
| Zinc pyridinethione crystals of Ex. I of USP 4,345,080 | 2.0 |
| Coconut monoethanolamide | 3.0 |
| Ethylene glycol distearate | 5.0 |
| Sodium citrate | 0.5 |

-continued

| Component | Level |
|---|---|
| Citric acid | 0.2 |
| Color solution | 0.1 |
| Perfume | 0.5 |
| Endo-H | 100 ppm |
| Bovine Lysozyme** | 100 ppm |
| Dimethylol dimethyl hydantoin | 0.05% |
| Water | q.s. 100% |

**4.0 units/microgram ±25%

This antidandruff shampoo composition remains free from bacterial or fungal contamination to a greater degree and/or for a longer period of time than a formula without the Endo-H/bovine lysozyme.

EXAMPLE VII

Liquid Soap

A liquid soap composition of the present invention is as follows:

| Component | Active Weight % |
|---|---|
| Ammonium lauryl sulfate | 6.0 |
| Sodium alkyl sarcosinate | 5.7 |
| Cocoamidopropyl betaine | 6.3 |
| Coconut fatty acid | 1.0 |
| Ethylenediamine tetraacetic acid | 0.2 |
| Ammonium sulfate | 0.4 |
| Perfume | 0.25 |
| Dye | 5 ppm |
| Water | 80.15 |
| Endo-H | 50 ppm |
| Bovine Lysozyme** | 50 ppm |

**4.0 units/microgram ±25%

The ingredients listed above are added to a mixer tank with a single agitator in the order in which they appear above. Before the enzymes, dye and perfume are added, the pH of the mix is adjusted so that a 10% by weight solution in water at 20° C. has a pH of about 6.5.

This composition provides antimicrobial action for the removal of common skin flora.

EXAMPLE VIII

Tablet Denture Cleaner

Sodium bicarbonate, sodium perborate monohydrate, tartaric acid, sodium tripolyphosphate, sulphamic acid, polyethylene glycol (20M) and ethylene diamine tetraacetate are separately granulated by fluidizing in a hot air bed at 60°-65° C. for 30 minutes. Such granulates are then tumble mixed with the other ingredients to produce a "first layer" mixture and a "second layer" mixture, wherein the "first layer" mixture has the following compositions:

| | % by Weight |
|---|---|
| Sodium bicarbonate | 30.00 |
| Tartaric acid | 23.00 |
| Potassium monopersulphate | 16.00 |
| Sulphamic acid | 11.00 |
| Disodium pyrophosphate | 8.20 |
| Sodium carbonate | 3.90 |
| Polyethylene glycol (20 M) | 2.60 |
| Sodium sulphate | 2.00 |
| Peppermint powder | 1.50 |
| Silicon dioxide | 1.30 |
| Sodium dodecyl benzene sulphonate | 0.50 | and the "second layer" mixture has the following composition:

| | % by Weight |
|---|---|
| Sodium perborate monohydrate | 30.00 |
| Potassium monopersulphate | 28.00 |
| Sodium bicarbonate | 13.34 |
| Sodium tripolyphosphate | 10.00 |
| Sodium bicarbonate/colour | 4.00 |
| Trilon B | 3.00 |
| Sodium carbonate | 3.00 |
| Polyethylene glycol (20 M) | 2.50 |
| Silicone dioxide | 2.00 |
| Peppermint powder | 1.50 |
| Wasag ester | 1.40 |
| Hardened triglycerides | 0.50 |
| Sodium dodecyl benzene sulphonate | 0.40 |
| Succinate detergent | 0.30 |
| Dye | 0.06 |
| Endo-H | 100 ppm |
| Bovine Lysozyme** | 100 ppm |

**4.0 units/microgram ±25%

A tablet is produced by compressing in a HORN rotary tableting press of 39 stations. Compressing is in two stages. Initially the "second layer", blue mixture is compressed to very low pressure (10 kN per tablet) by way of tamping. The "first layer", white mixture is then instilled and pressed to 70 kN per tablet. In this way a tablet of 4 grams is produced, which contains 2.7 grams blue and 1.3 grams white.

Tablets are dissolved in water by the consumer and dentures are cleaned by placing them in the water containing the denture cleaner and then rinsing them.

Modifications of the above preferred embodiments which are obvious to a person of ordinary skill in the art are intended to be within the scope of this invention.

What is claimed is:

1. An antibacterial composition having a pH between 6.5 and 8.5 in a 10% by weight solution in water at 20° C., comprising ruminant stomach lysozyme, and endo-$\beta$-N-acetylglucosaminidase or endoglycopeptidase in a weight ratio of from about 1:4 to 4:1; wherein said endo-$\beta$-N-acetylglucosaminodase is Endo-F, Endo-D or Endo-H, or said endoglycopepidase is PNGase F or PNGase A.

2. The antimicrobial composition of claim 1 wherein said ruminant stomach lysozyme is one or more ruminant stomach lysozymes c.

3. The antimicrobial composition of claim 2 wherein the weight ratio of ruminant stomach lysozyme c to endo-$\beta$-N-acetylglucosaminidase or endoglycopeptidase is from about 2:1 to 1:2.

4. The antimicrobial composition of claim 2 comprising from about 1 to 1000 ppm of said ruminant stomach lysozyme c and from about 1 to 1200 ppm endo-$\beta$-N-acetylglucosaminidase or endoglycopeptidase.

5. The antimicrobial composition of claim 4 comprising bovine lysozyme c2 and Endo-H or PNGase F.

6. The antimicrobial composition of claim 5 comprising from about 50 to 400 ppm each of said bovine lysozyme and said Endo-H or PNGase F.

7. The antimicrobial composition of claim 6 comprising recombinant bovine lysozyme c2, and Endo-H.

8. The antimicrobial composition of claim 7 wherein the weight ratio of said recombinant bovine lysozyme to Endo-H is from about 2:1 to 1:2.

9. The antimicrobial composition of claim 8 comprising from 50 ppm each of Endo-H and said recombinant bovine lysozyme from *Pichia pastoris*.

10. The antimicrobial composition of claim 4 wherein said composition is selected from the following: mouthwash, denture cleaner, dentifrice, laundry detergent, preservative, contact lens cleaner, liquid soap, and skin cleanser.

11. The antimicrobial composition of claim 4 further comprising from about to 90 weight % detergent surfactant selected from the group consisting of anionic, nonionic, cationic, ampholytic and zwitterionic surfactants.

12. The antimicrobial composition of claim 5 wherein said composition is a mouthwash, denture cleaner or dentifrice comprising from about 1 to 150 ppm each of Endo-H or PNGase F and bovine lysozyme c2.

13. The antimicrobial composition of claim 7 wherein said composition is a liquid or granular laundry detergent comprising from about 2 to 250 ppm each of Endo-H and recombinant bovine lysozyme c2, and from about 5 to 50 weight % of detergent surfactant selected from the group consisting of anionic, nonionic, cationic, ampholytic and zwitterionic surfactants.

14. The antimicrobial composition of claim 6 wherein said composition is a preservative for a shampoo or cosmetic.

15. The antimicrobial composition of claim 6 wherein said composition is a liquid hand soap further comprising from about 10 to 40 weight % of detergent surfactant selected from the group consisting of anionic, nonionic, cationic, ampholytic and zwitterionic surfactants.

16. The antimicrobial composition of claim 9 wherein said composition is a skin cleaner.

17. A method for the destruction or removal of microbes by application of a composition having a pH between 6.5 and 8.5 in a 10% by weight solution in water at 20° C. comprising ruminant stomach lysozyme and endo-$\beta$-N-acetylglucosaminidase or endoglycopeptidase in a weight ratio of from about 1:4 to 4:1, wherein said endo-$\beta$-N-acetyl glucosaminidase is Endo-F, Endo-D or Endo-H, or said endoglycopeptidase is PNGase F or PNGase A.

18. The method of claim 17 wherein said composition comprises ruminant stomach lysozyme c.

19. The method of claim 18 wherein the weight ratio of said ruminant stomach lysozyme c to said endo-$\beta$-N-acetylglucosaminidase or said endoglycopeptidase in said composition is from about 2:1 to 1:2.

20. The method of claim 18 wherein said composition comprises bovine lysozyme c2, and Endo-H or PNGase F.

21. The method of claim 20 wherein said composition comprises Endo-H or PNGase F, and recombinant bovine lysozyme from *Pichia pastoris*.

22. The method of claim 21 for the destruction or removal of bacteria wherein said composition comprises from about 1 to 1200 ppm Endo-H and from about 1 to 1000 ppm of said recombinant bovine lysozyme.

23. The method of claim 22 for the destruction or removal of *Staphylococcus aureus* or *Escherichia coli* wherein said composition comprises from about 50 to 400 ppm each of said recombinant bovine lysozyme and Endo-H.

24. The method of claim 22 wherein the weight ratio of said recombinant bovine lysozyme to Endo-H in said composition is from about 1:2 to 2:1.

25. The method of claim 24 wherein said composition comprises from about 100 to 150 ppm each of Endo-H and said recombinant bovine lysozyme.

* * * * *